United States Patent
Falconer

(10) Patent No.: US 7,160,275 B2
(45) Date of Patent: Jan. 9, 2007

(54) OSTOMY POUCHES

(75) Inventor: Malcolm I. Falconer, Clone West (IE)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 10/780,240

(22) Filed: Feb. 17, 2004

(65) Prior Publication Data

US 2005/0015065 A1 Jan. 20, 2005

Related U.S. Application Data

(62) Division of application No. 09/370,305, filed on Aug. 9, 1999, now Pat. No. 6,709,421.

(30) Foreign Application Priority Data

Aug. 13, 1998 (GB) ................................. 9817677.9

(51) Int. Cl.
*A61F 5/44* (2006.01)

(52) U.S. Cl. ...................... 604/333; 604/338

(58) Field of Classification Search ................ 604/277, 604/327–344, 355; 55/385.4; D24/118, D24/121, 122
See application file for complete search history.

(56) References Cited

U.S. PATENT DOCUMENTS

| | | | | |
|---|---|---|---|---|
| 3,439,677 | A | * | 4/1969 | Bonfils ........................ 604/333 |
| 3,604,421 | A | * | 9/1971 | Pizzella ...................... 604/335 |
| 4,252,120 | A | * | 2/1981 | Carpenter .................. 604/336 |
| 4,372,308 | A | * | 2/1983 | Steer et al. ................. 604/333 |
| 4,449,970 | A | * | 5/1984 | Bevan et al. ............... 604/333 |
| 4,490,145 | A | * | 12/1984 | Campbell .................... 604/333 |
| 4,668,258 | A | * | 5/1987 | Steer ............................. 96/12 |
| 4,681,574 | A | | 7/1987 | Eastman |
| 4,938,750 | A | * | 7/1990 | Leise, Jr. ..................... 604/333 |
| 5,591,144 | A | * | 1/1997 | Smith et al. ................. 604/327 |
| 5,690,622 | A | * | 11/1997 | Smith et al. ................. 604/333 |
| 5,690,623 | A | * | 11/1997 | Lenz et al. .................. 604/333 |
| 5,865,819 | A | * | 2/1999 | Cisko et al. ................. 604/339 |
| 5,938,647 | A | * | 8/1999 | Smith .......................... 604/332 |
| 5,976,118 | A | * | 11/1999 | Steer .......................... 604/332 |
| 6,129,716 | A | * | 10/2000 | Steer .......................... 604/333 |
| 6,165,159 | A | * | 12/2000 | Blanton ....................... 604/333 |
| 6,171,288 | B1 | * | 1/2001 | Wiltshire ..................... 604/333 |
| D460,550 | S | * | 7/2002 | Falconer ..................... D24/118 |

(Continued)

FOREIGN PATENT DOCUMENTS

DE  19519069 A  11/1996

(Continued)

*Primary Examiner*—Tatyana Zalukaeva
*Assistant Examiner*—Michael G. Bogart
(74) *Attorney, Agent, or Firm*—Stuart E. Krieger

(57) ABSTRACT

An ostomy pouch (10) includes a front wall (12) provided with a comfort layer (16) and a vent (22). An apertured cover layer (24) is secured to the front wall (12) through the comfort layer (16) to define a chamber for a filter element (28) and to provide a smooth surface to which can be applied an adhesive sticker. The cover layer (24) includes a plurality of apertures (30), and the flow rate through the vent can be controlled by positioning the sticker to selectively block one or more of the apertures (30). An adhesive wafer (40) includes both circular and non-circular (race-track) cut-out guidelines for enabling the aperture to be cut to any desired shape and size. The wafer (40) is secured to the pouch along a weld line having a shape corresponding to a combined circular and race-track silhouette.

16 Claims, 9 Drawing Sheets

U.S. PATENT DOCUMENTS 6,659,989 B1 * 12/2003 Otto ........................... 604/344
6,709,421 B1 * 3/2004 Falconer ..................... 604/335

FOREIGN PATENT DOCUMENTS

| EP | 0 231 508 | * | 7/1986 |
| EP | 0 231 508 A2 | * | 8/1987 |
| EP | 0 276 042 | * | 7/1988 |
| EP | 0 276 042 A2 | * | 7/1988 |
| EP | 0535801 A1 | | 4/1993 |
| EP | 0 535 801 | * | 7/1993 |
| EP | 0868892 A | | 10/1998 |
| GB | 2273052 A | | 6/1994 |
| WO | WO 98/17212 A | | 4/1998 |
| WO | WO 98/53771 A | | 12/1998 |

* cited by examiner

OSTOMY POUCHES

This is a division of Ser. No. 09/370,305, filed Aug. 9, 1999, now U.S. Pat. No. 6,709,421.

The present invention relates to ostomy pouches for the collection of waste, or discharge, from a temporary or permanent ostomy opening. The invention is applicable equally to so-called one piece designs in which the pouch is integral with an attachment pad or wafer for attaching the pouch to the body of the ostomate, and with so-called two-piece designs in which the pad or wafer for securing the pouch to the ostomate is separate from, and is releasably attachable to, the pouch.

One aspect of the invention relates to a filtered flatus vent which is commonly provided in certain ostomy pouches. The vent allows flatus gas within the pouch to escape, in order to avoid ballooning of the pouch. A sticker is sometimes provided which is initially adhered over the exit from the vent in order to prevent, initially, any gas from flowing through the vent. The purpose of this is, when the pouch is first worn, to allow some gas to build up within the pouch and thereby prevent the sides of the pouch from sticking to each other, which could cause undesirable pancaking. Once the pouch has begun to inflate (and the sides separated from each other), the sticker can be removed in order to allow flatus to vent in the normal way.

In one broad aspect, the invention provides a filtered vent for an ostomy pouch having a plurality of outlets, and adhesive sticker means which can be positioned to selectively expose or cover one or more of the plurality of outlets.

This aspect can provide a very simple, yet, convenient way of allowing the user to control the flow rate of flatus passing through the vent. This is in contrast to the prior art in which the sticker and the single exit can provide only on/off control. When the sticker is removed, if the flow rate of gas through the filter is too high (depending on a particular person's metabolism and on the food consumed), the sides of the pouch may tend to stick to each other again, and cause pancaking. However, with this aspect of the present invention, the ostomate can selectively cover, or uncover, a desired number of the outlets to control the rate at which flatus vents, and thereby control the degree of pouch inflation to prevent pancaking.

In one embodiment, the sticker means might be dimensioned so that it is of sufficient size to be able to cover all the outlets (when positioned appropriately) and can expose one or more of the exits by being moved to an offset position.

In an alternative embodiment, the patch means may consist of a number of separable sticker segments which can be peeled away to selectively expose one or more exits under each segment.

In a yet further form, the sticker means may comprise a plurality of individual stickers each of which can be attached, or removed, from a respective exit.

The exits may be in the form of slits, or other apertures, formed in a plastics film covering, for example, the filter. Alternatively, the exits may be in the form of clearances between one or more welds, or weld segments.

If desired, a flow constricting layer may be provided upstream of the outlets (for example, under a plastics layer having outlet apertures). This can allow the apertures to be made larger, and more easily identifiable, without such critical dependency on aperture size.

In a further aspect, the invention provides a vent for an ostomy pouch, the vent comprising aperture means, a flow constricting layer upstream of the aperture means, and adhesive sticker means which can be positioned to selectively block one or more areas of the aperture means.

The presence of the flow constricting layer can enable larger aperture(s) to be used because the flow is constricted by the layer. The aperture may either be a single aperture (for example, a relatively large aperture), or a plurality of individual apertures.

The flow constricting layer may, for example, consist of micro-porous material. The layer might, in some embodiments, by formed by a filter element.

In a further aspect, the invention relates to an ostomy pouch having a so-called comfort layer. Such a comfort layer is generally soft and permeable, and is provided outside the non-permeable plastics wall of the pouch to provide more comfortable wearing characteristics. Customers generally prefer a comfort layer to be provided on both the rear face (i.e. adjacent to the skin) and on the front face (i.e. facing the wearer's clothing).

In this aspect, the invention provides an ostomy pouch in which a first wall of the pouch is provided with a comfort layer and with a flatus vent, the pouch further comprising adhesive sticker means attached, or attachable to the vent to control the flow of flatus through the vent.

Preferably, the outlet of the vent is defined by at least one segment of smooth, substantially impermeable, plastics material positioned outside the comfort layer. This can provide surface with excellent characteristics to allow the adhesive sticker means to adhere to provide a gas-tight. (or at least substantially gas-tight) seal, and thereby enable the sticker to control the flow of gas through the vent. To the best of the inventor's knowledge, it is unknown hitherto to employ a sticker for a vent through a wall carrying a comfort layer. In particular, it might difficult to achieve a gas-type seal if the sticker is applied directly to the comfort layer. In the preferred embodiment, the provision of the smooth plastics material outside the comfort layer can overcome this problem.

As explained previously, there is a need for some form of device, at least initially, to block or constrict the flow of flatus through the vent, in order to prevent pancaking. The ability to provide a simple adhesive sticker means with a comfort-layer adorned pouch is an extremely significant advantage.

Preferably, the comfort layer is provided outside the majority of at least the upper portion of the pouch. Preferably, the smooth material described above overlies a portion of the comfort layer, and is secured to the underlying wall of the pouch through the comfort layer (for example, by welding, or by adhesive).

Preferably, the smooth material outside the comfort layer forms an outer cover for the filter, and is secured to the underlying pouch wall around the filter. The line of attachment (e.g. welding) may be continuous, or it may be discontinuous to provide one or more vent exits.

In another aspect, the invention relates to the construction of a filtered vent for an ostomy pouch which has a comfort layer.

In this third aspect, the invention broadly provides an ostomy pouch comprising a first wall of substantially liquid and gas impermeable plastics material, an aperture being provided in the first wall to allow the venting of flatus, a comfort layer provided outside the first wall, and a filter cover layer outside the comfort layer and secured to the first wall through the comfort layer, the cover layer and the portion of the first wall underlying the cover layer defining a housing in which is received a filter for processing the flatus vented through the aperture.

The filter may, for example, include material for deodorising the flatus, and/or material for absorbing any liquid which accidentally escapes through the aperture in the first wall.

The filter may be positioned between the first wall and the comfort layer. In that case, the filter is preferably attached to the first wall, to provide a seal around the aperture in the first wall. Alternatively, the filter may be provided between the comfort layer and the cover layer. In that case, the filter may either be attached to the cover layer, or it may be attached to the first wall.

A yet further aspect of the invention relates to the adhesive wafer which is provided conventionally for securing the pouch to the wearer's skin.

In accordance with this broad aspect, the wafer (or a cover layer provided on the wafer) is provided with guidelines for enabling a person to cut the wafer to a desired aperture size, the guidelines including at least one generally circular guideline, and at least one generally non-circular guideline.

Preferably, the non-circular guideline is a so-called race-track guideline, defining a shape having generally straight sides, and rounded ends.

Preferably, a plurality of circular, and a plurality of non-circular, guidelines are provided.

This aspect of the invention can facilitate the same pouch being usable for a conventional ostomy application (where the aperture is normally circular) and also for other applications, including temporary ostomy (for example, loop ostomy) applications. For a temporary ostomy application, a more elongate aperture is desired to accommodate a temporary fold in the ostomate's intestines.

To the best of the inventor's knowledge, hitherto pouches have only been available exclusively with circular guidelines, or exclusively with race-track guidelines. This has meant that a specific pouch has to be obtained to suit the desired application. However, with the present invention, a single pouch can be provided which a user can adapt very easily to the correct circular, or non-circular aperture size.

This aspect of the invention can be used either in a one-piece pouch design, or in a two-piece pouch design. Especially (but not exclusively) for the one-piece design, it is preferred that the wafer is secured to the pouch (or pouch coupling member) by means of a weld or glue line having a non-circular and non-race-track shape. Preferably, the shape is defined by a combination of a circular shape and a race-track shape, the shape corresponding to a silhouette of one superimposed on the other.

The use of such a weld (or glue) line might be the most efficient shape for accommodating a large circular, or race-track cut out, without requiring the adhesive wafer to be unnecessarily large.

Preferably, the wafer also has a "hybrid" outer shape based generally on the silhouette of a circular shape and a race-track shape superimposed one on the other.

It will be appreciated that the guidelines might be provided (by printing) directly on the adhesive wafer, or they may be provided on a release sheet which protects the adhesive surface of the wafer before use. The release sheet is intended to be peeled away before the adhesive wafer is pressed against the skin.

Although the above aspects may be used independently of each other, further benefits can arise by combining two or more of the above aspects in combination. The invention contemplates that any of the above aspects may be used in combination.

Embodiments of the invention are now described, by way of example only, with reference to the accompanying drawings, in which.

Figure 1:
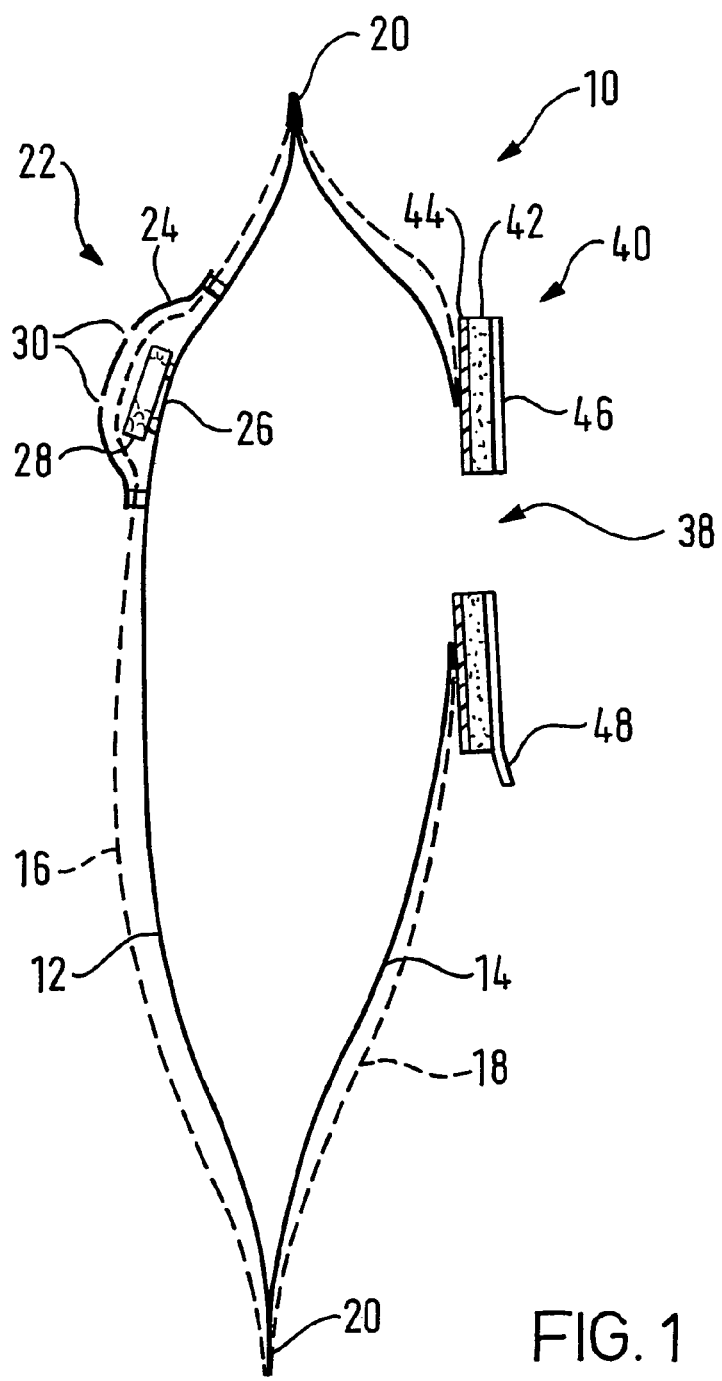
FIG. 1 is a sectional through a first embodiment of an ostomy pouch.
Figure 2:
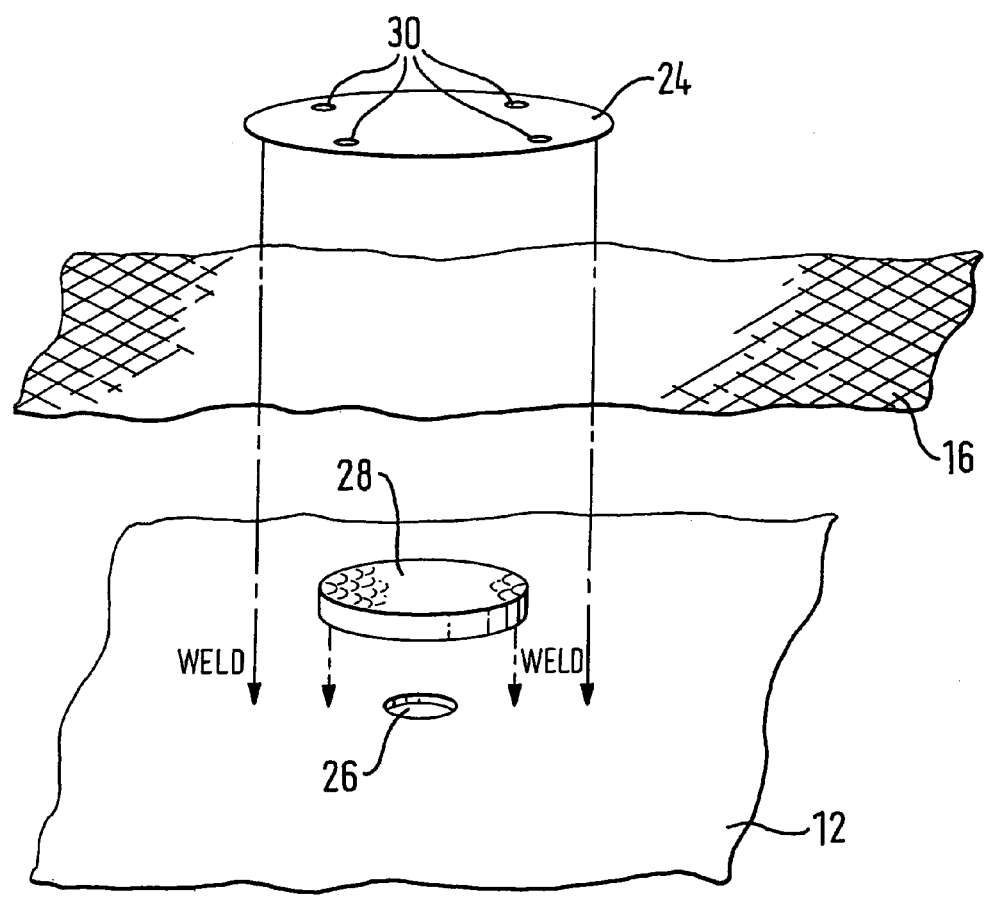
FIG. 2 is a schematic exploded view showing the construction of the filter and filter housing

Referring to FIGS. 1–5, and ostomy pouch 10 includes an envelope formed by a frontwall 12 and a rear wall 14 both of plastics material which is substantially impervious to liquid and to gas. Such plastics materials are well known in the art, and typically may consist of a laminate of one or more layers of ethylene vinyl acetate (EVA) on either side of a barrier layer of polyvinylidine chloride (PVDC). Other materials may be used as desired.

A front comfort layer 16 is positioned outside the front wall 12, and a rear comfort layer 18 is positioned outside the rear wall 14. The comfort layers are generally soft and are permeable to gas and to liquid. Typically the comfort layers are made of Nylon, or polyethylene, or a mixture of polyester, viscous and rayon.

The front and rear walls 12 and 14 and the comfort layers 16 and 18 are secured to each other by welding around a peripheral seam 20. The welding may be performed by an RF welding head, for example. Alternatively the seam may be formed by impulse welding, or by a heat seal and cut process.

A filter housing 22 is located towards an upper portion of the front wall 12. The housing is formed by a filter cover 24 which is secured through the front comfort layer 16 to the front wall 12 in a generally gas-tight manner. In the present embodiment, the filter cover 24 is attached by welding, and the heat generated by welding is sufficient to at least partly melt the comfort layer in order to perform a reliable seal between the filter cover 24 and the front wall 12. The filter cover may, for example, be made of the same material as the front and rear walls 12 and 14.

An aperture 26 is formed in the front wall 12 under the filter cover 24, and a filter element 28 is secured to the front wall 12 over the aperture 26. In this embodiment, the filter is a deodorising filter for deodorising flatus gas, and includes a deodorising agent, such as carbon. The filter may consist of foam carrying the carbon, or it may consist of other material, such as charcoal cloth. If desired, the filter may also include additional agents, such as a super absorbent agent for absorbing any liquid which leaks accidentally through the aperture 26.

A suitable deodorising filter is manufactured by Freudenberg Limited, for example under the reference "option 20".

Although the filter is illustrated to lie between the front wall 12 and front comfort layer 16, it will be appreciated that in other embodiments, the filter could be positioned between the filter cover 24 and the comfort layer 16, or on the other side of the front wall 12 (i.e. inside the envelope). The filter would need to be sealed to at least one of the front wall 12 and the filter cover 24, in order to prevent flatus leaking around the outside of the filter element 28.

A plurality of gas exits 30 are formed in the filter cover 24. In the preferred embodiment, the exits 30 are relatively small (pin-hole) apertures in the filter cover 24. The number of apertures may be varied as desired; in the present embodiment, four apertures are illustrated.

Figure 3:
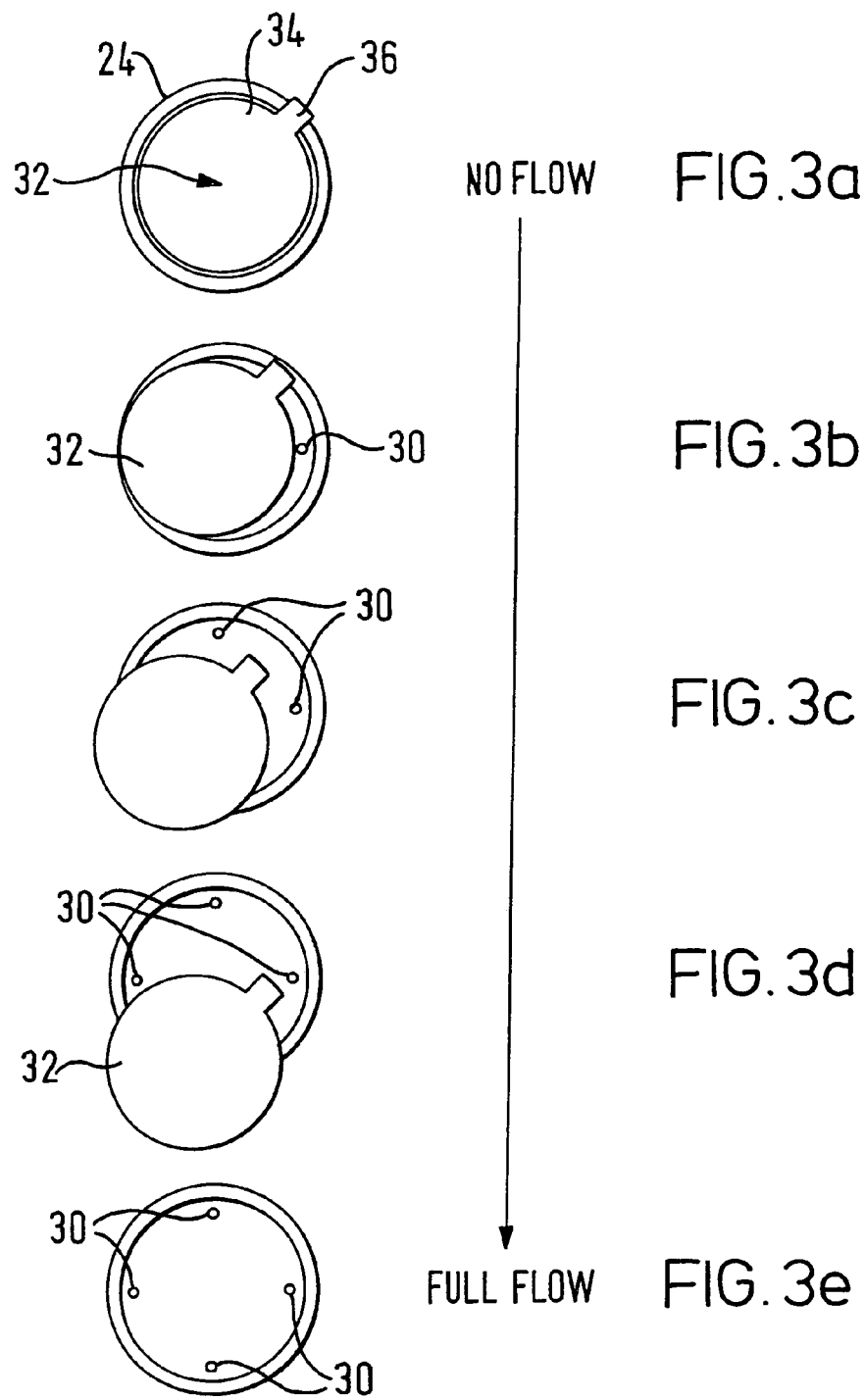
FIGS. 3a–3e are schematic plan views showing adjustment of the sticker for flow control.

One or more of the apertures 30 may be selectively blocked by means of an adhesive sticker 32. As best seen in FIG. 3 the sticker consists of a main circular portion 34, and a finger tab 36 to enable the sticker to be grasped and peeled from the surface of the filter cover 24.

The combination of the plurality of apertures 30 and the sticker 32 enables the user to control the rate of the flow of gas through the vent and the filter. As best seen in FIG. 3a, the size of the main circular portion 34 is sufficient to enable the sticker, when positioned appropriately, to block all four of the apertures 30. This completely cuts off flow through the filter vent.

As illustrated in FIGS. 3b–3e, by positioning the sticker 30 appropriately, 1, 2, 3 or all 4 of the apertures 30 may be exposed to allow a progressive increase in the flow rate through the filter vent. Such use of the sticker can provide the user with an extremely powerful, yet easy to use, flow control.

Moreover, it will be appreciated that the use of material (in this case the filter cover 24) outside the front comfort layer 16 enables a sticker to be applied to achieve a substantially gas tight sticker seal. The sticker might be virtually ineffective if it were applied directly to the porous comfort layer.

Figure 4:
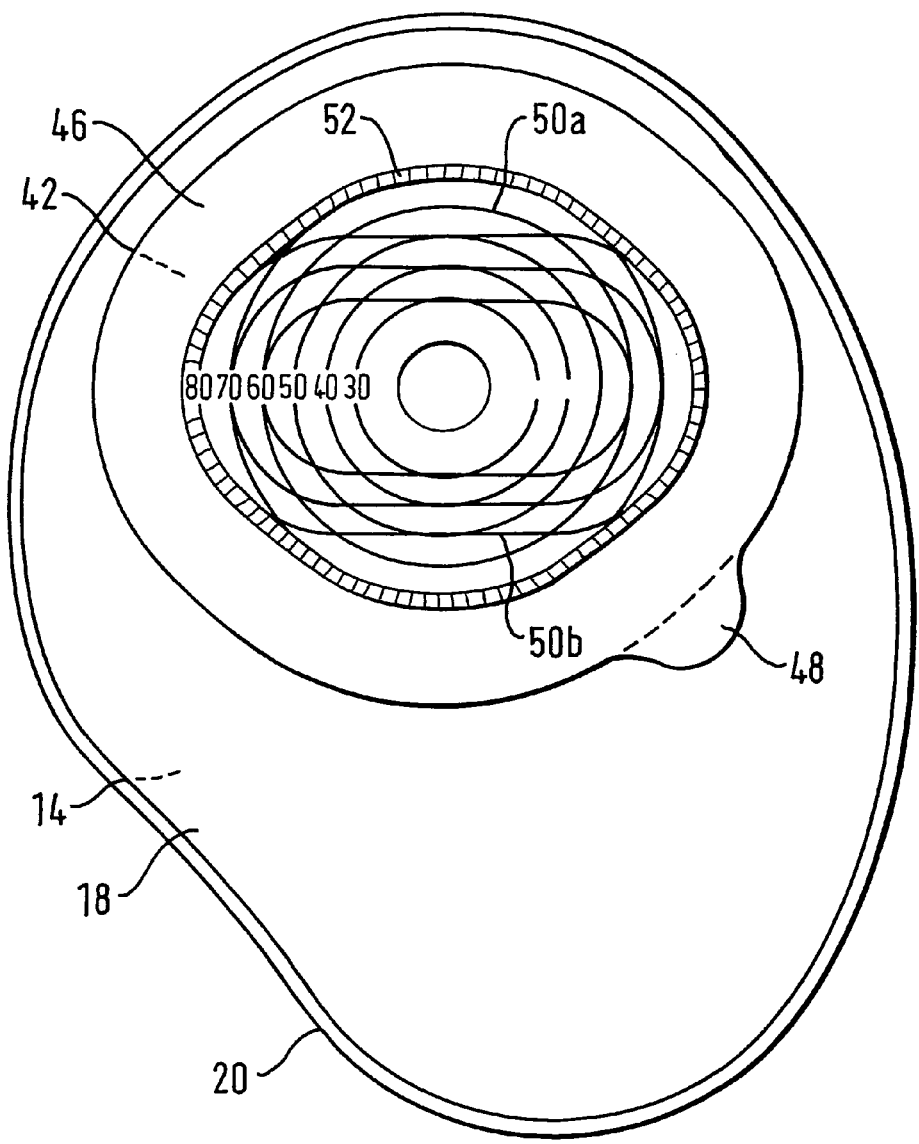
FIG. 4 is a rear view of the pouch of FIG. 1.
Figure 5A:
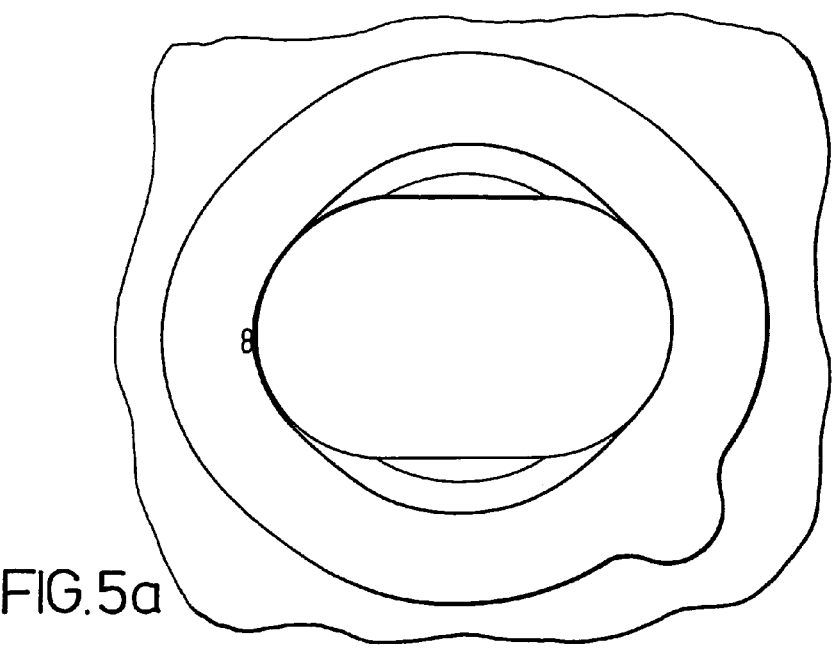
FIGS. 5a and 5b illustrate different cut outs of aperture in the wafer shown in FIG. 4.
Figure 5B:
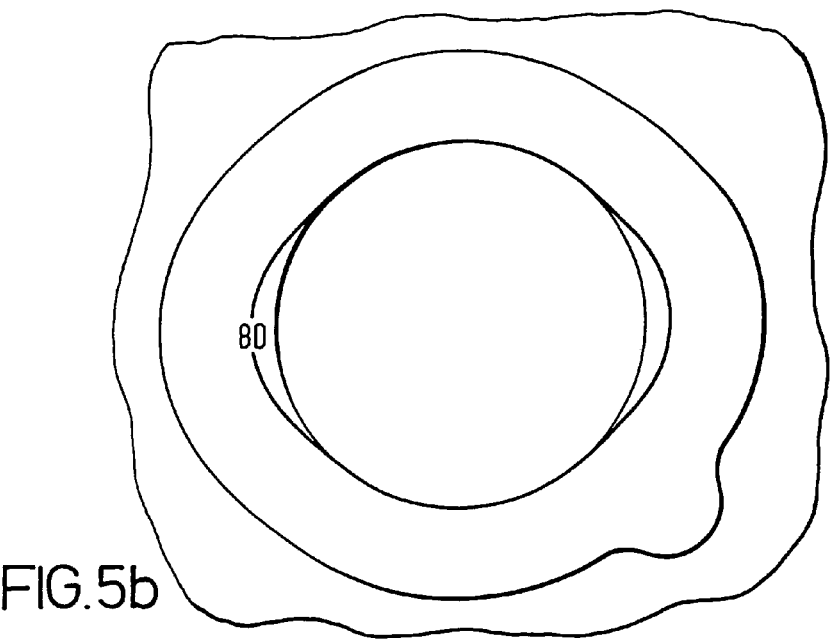

Referring to FIGS. 1 and 4, the rear wall 14 and the rear comfort layer 18 include a stoma aperture 38 for receiving the ostomate's stoma, and for allowing the stomal discharge into the envelope. Attached to the rear wall 14, and encircling the stomal aperture 38 is an adhesive wafer 40 for allowing the pouch to be secured to the ostomate's skin.

The wafer 40 consists generally of a layer of skin-compatible adhesive 42, a backing layer 44 of plastics material welded to the rear wall 14, and a silicone release sheet 46 having a finger tab 48 by which the release shut 46 can be peeled away from the adhesive 42 to expose the adhesive face. As best seen in FIG. 4, the release sheet 46 is printed with guidelines 50, (50a and 50b) for enabling the user to cut the wafer to a desired aperture size prior to fitting. This may either be carried out by the ostomate, or by a supervising nurse or other medical practitioner.

In this embodiment, the guidelines include circular guidelines 50a and non-circular (race track) guidelines 50b. The circular guidelines 50a define a range of circular shaped apertures of different sizes, to suite permanent stomas, which generally have a circular or near-circular configuration. The race track guidelines 50b define a number of elongate apertures of different sizes, suitable for temporary stomas (e.g. stomas formed in a loop-ostomy operation, in which a portion of the intestine is extracted and is folded around a suitable rod, and is "sliced" open to define an elongate temporary stoma).

As mentioned above, the backing layer 44 is welded to the rear wall 14. The weld line is illustrated in FIG. 4 by the shaded region 52. The weld line 52 defines a shape which is a silhouette of a circular shape superimposed on a race track shape. On this embodiment, the weld line 52 corresponds to the silhouette surrounding the largest permissible circular cut out, and the largest permissible race track cut out. The use of such a special shape of weld line 52 can provide a more versatile pouch design, enabling large circular cut outs (e.g. see FIG. 5a), and large race track cut outs (e.g. see FIG. 5b), to be accommodated without unnecessarily increasing the size of the wafer, or the size of the weld line between the wafer 40 and the pouch 10.

As illustrated in FIG. 4, the overall shape of the wafer 40 is similar to the shape of the weld line 52, and corresponds to the silhouette of a circular shape superimposed on a racetrack shape.

Figure 6:
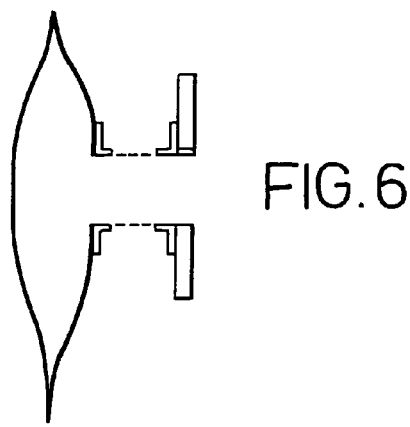
FIG. 6 illustrates a modified pouch and wafer with a mechanical coupling.

Although the above embodiment is a one-piece pouch, it will be appreciated that the same principles could be applied to a two-piece pouch (FIG. 6) in which the adhesive wafer 40 is not permanently fixed to the remainder of the pouch, but is a separate element 58 which is releasably attachable to the pouch, for example, by a mechanical coupling, or an adhesive coupling. Such couplings are well known in the art, and need not be described further here.

Figure 7A:
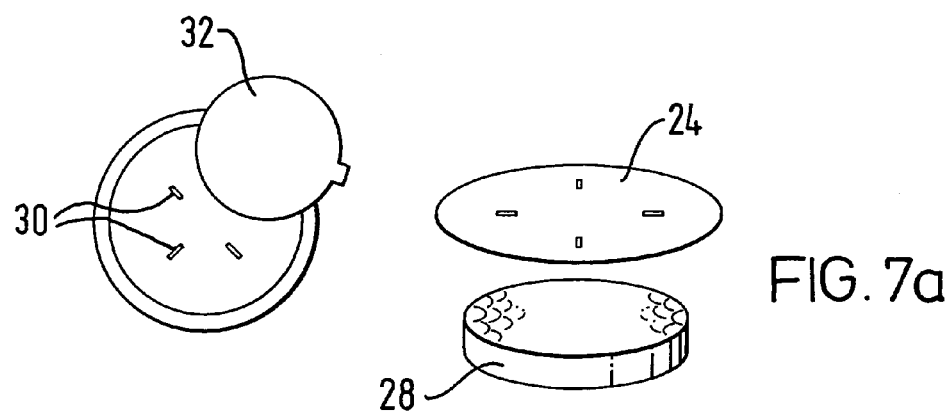
FIGS. 7a and 7b are schematic views showing a modified design of filter cover.
Figure 7B:
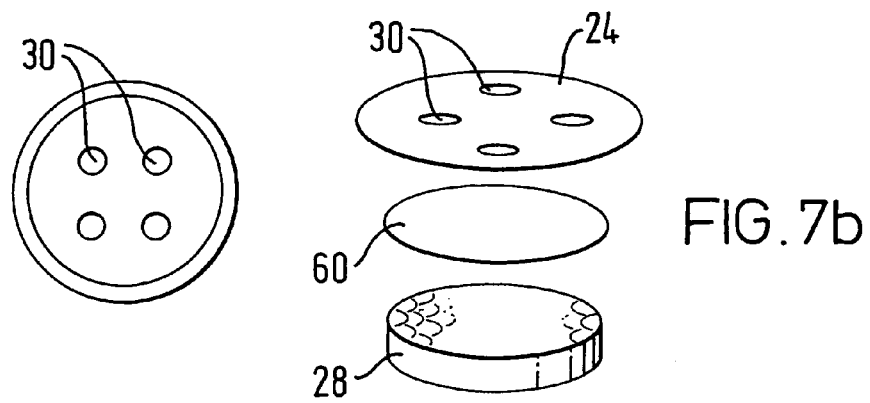

FIGS. 7a and 7b illustrate, in one form, the relationship between the size of apertures in the filter cover 24, and the need for the apertures to provide a constriction to the flow rate. It will be appreciated that, in order to achieve an adjustable flow, each individual aperture must provide a constriction to the flow of flatus gas. This can be achieved by making the apertures 30 suitably small, for example, in the form of slits (FIG. 7a). Alternatively, a flow constricting layer 60 may be provided under the filter cover 24 to constrict the flow through each aperture 30. This would allow the use of much large apertures 30, making them easier to identify than if narrow slits were to be used. A suitable constriction layer is of microporous material.

Figure 8A:
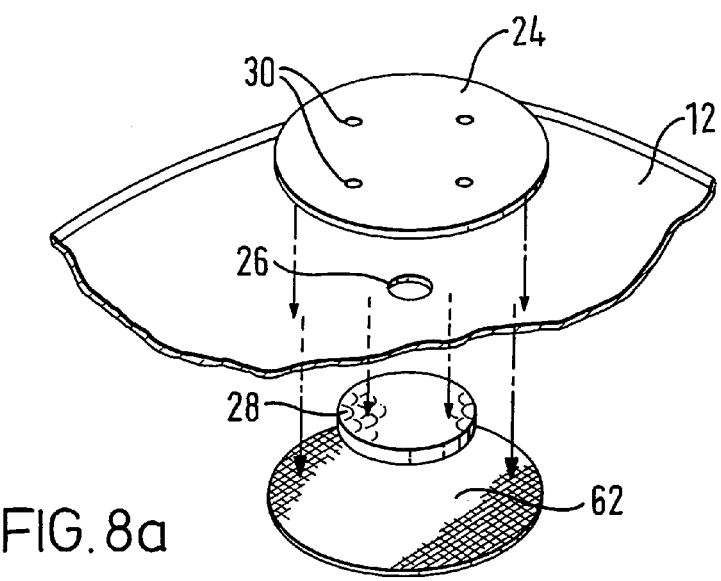
FIGS. 8a and 8b illustrate an alternative construction of filter.
Figure 8B:
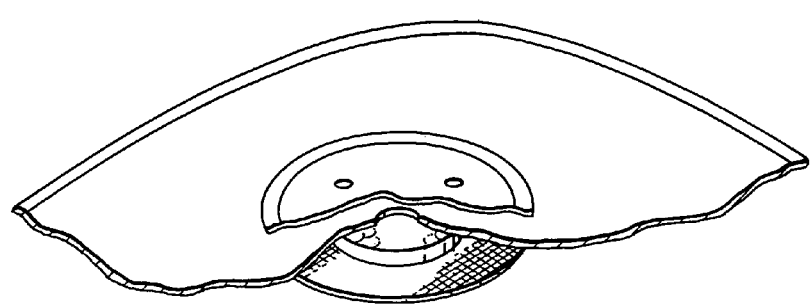

FIGS. 8a and 8b illustrate a modified construction of filter without the presence of a comfort layer. In this embodiment, the filter element 28 is located inside the envelope, on the inside face of the front wall 12. The aperture 26 in the front wall 12 is typically about 8–10 mm in diameter. To allow the use to control the flow with a sticker, the filter cover 24 (now referred to simply as a outer cover 24) is attached to the outer face of the front wall 12, and is provided with small pin-holes 30. The size of each pin-hole 30 is sufficiently small to constrict the flow of flatus through the apertures when one or more of the apertures is covered by the sticker 32. If desired, a constriction layer (not shown) similar to the constriction layer 60, may be provided under the cover layer 24 if larger, more easily identifiable, apertures 30 are required.

In this embodiment, since the filter element 28 is located inside the envelope, it is preferred that a semi-porous protective membrane, or curtain, 62 be provided over the inner face of the filter, to prevent faecal matter in the pouch from directly contacting the filter element 28.

Figure 9A:
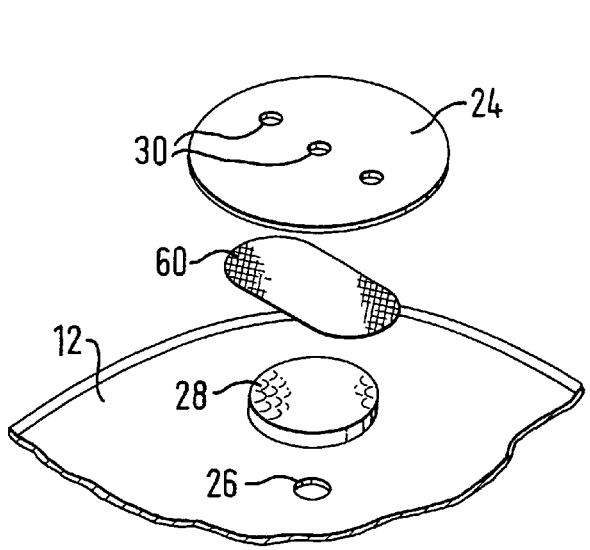
FIGS. 9a and 9b illustrate a yet further construction of filter.
Figure 9B:
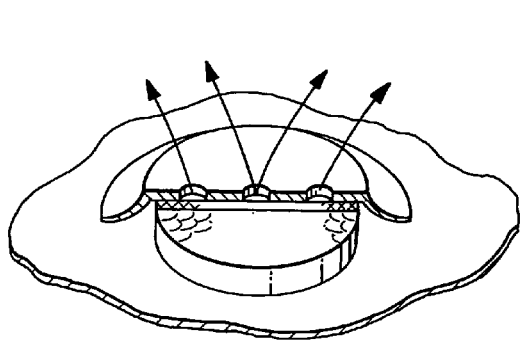

FIGS. 9a and 9b illustrate a further modified embodiment in which the filter element 28 is located outside the front wall 12 of the pouch. The cover layer 24 has three relatively large apertures 30 which are arranged in a generally straight line. A constriction layer 62 (micro-porous membrane) is located under the cover layer 24, in order to provide the required flow constriction for the size of aperture. Since the apertures 30 are arranged in a line, the constriction layer 62 is provided in the form of a narrow strip, in order to reduce wastage of material.

Figure 10A:
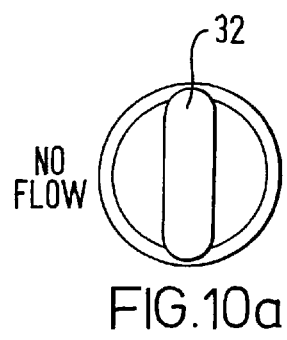
FIGS. 10a–10d illustrate schematically positioning of the sticker for controlling the flow through the filter of FIGS. 9a and 9b.
Figure 10B:
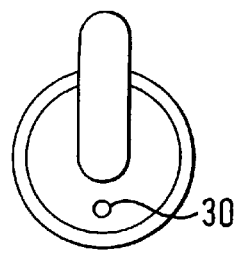
Figure 10C:
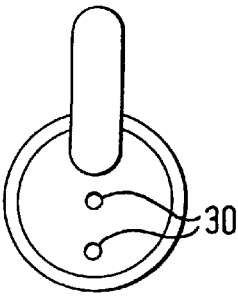
Figure 10D:
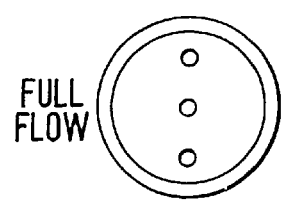

FIGS. 10a–10b illustrate the various positions of the sticker 32 over the apertures 30, to vary the flow from zero (FIG. 10a) to full flow (FIG. 10d).

Figure 11A:
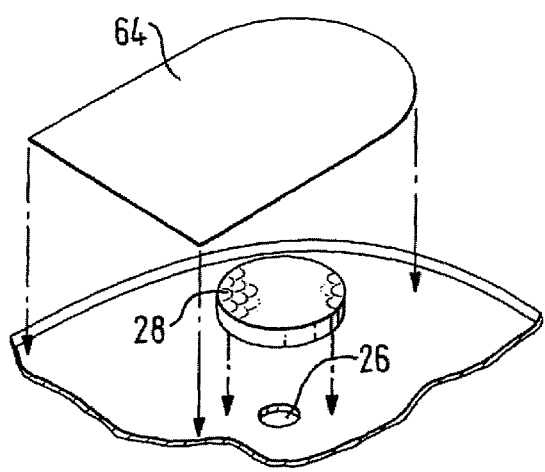
FIGS. 11a and 11b illustrate a further modified design of filter.
Figure 11B:
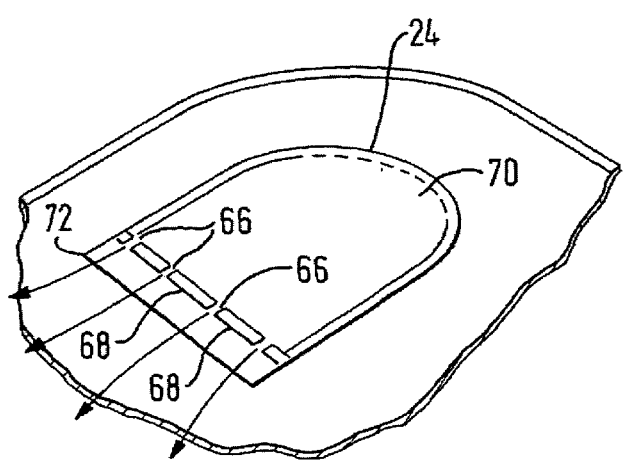
Figure 12E:
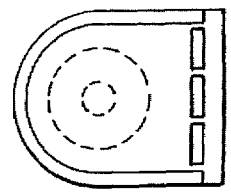
FIGS. 12a–12e illustrate schematically peeling of the sticker for controlling the flow through the filter of FIGS. 11a and 11b.
Figure 12D:
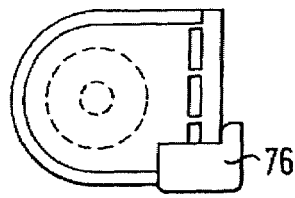
Figure 12C:
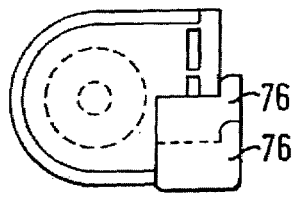
Figure 12B:
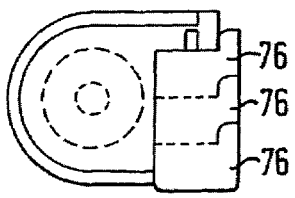
Figure 12A:
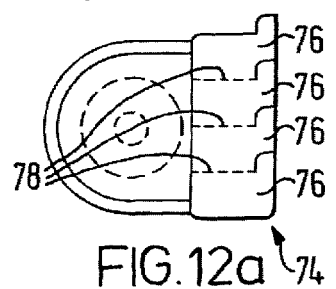

FIGS. 11a and 11b illustrate a yet further modified construction of filter housing. In contrast to the earlier embodiments in which the cover layer 24 is sealed completely around the filter element 28 and has apertures 30 through the cover layer 24, the present embodiment employs a completely impervious cover layer 64, and the vent exits are defined by gaps 66 between weld segments 68 securing the cover 24 to the front wall 12 of the pouch. In the present embodiment, the cover 24 is illustrated to have a rounded end 70 to match the contour around the filter and a square end 72 at which the gas exits 66 are defined.

FIGS. 12a–12e illustrate how the flow rate through the exits 66 can be controlled by means of a sticker 74. Although a single sticker could be used as in the previous embodiments, here a multiple-segment sticker 74 consisting of segments 76 is employed. The flow rate is controlled by peeling away individual segments 76 from the exits 66. The segments may be separate from each other, or they may be attached to each other by breakable perforations 78 to allow the segments to be torn away.

Although the embodiments illustrated in FIGS. 8–12 do not include a comfort layer, it will be appreciated that the embodiments may be modified to include a comfort layer using the same principles as described in the first embodiment.

It will be appreciated that many modifications of detail may be made without departing from the scope and principals of the invention. Although features believed to be of particular importance are defined in the appended claims, the applicant claims protection for any novel feature or idea described herein and/or illustrated in the drawings whether or not emphasis has been placed thereon.

What is claimed is:

1. An apparatus comprising a controllable flow rate, filtered, vent for an ostomy pouch, the vent having a plurality of outlets and a device for controlling the rate of flow of gas through the vent, the device comprising adhesive sticker means which can be positioned and re-positioned to selectively expose or cover one or more of the plurality of outlets, and thereby regulate variably the rate of flow of gas according to the outlets exposed, and an adhesive wafer for directly or indirectly securing the ostomy pouch to a person's skin, wherein the wafer, or a cover layer provided on the wafer, is provided with guidelines for enabling a person to cut the wafer to a desired aperture size, the guidelines including at least one generally circular guideline, and at least one generally non-circular guideline having a race-track shape.

2. The apparatus according to claim 1, wherein the flow rate is controllable according to the number of outlets exposed.

3. The apparatus according to claim 1, wherein the sticker means comprises a sticker dimensioned so that it is of sufficient size to be able to cover all of the outlets.

4. The apparatus according to claim 1, wherein one or more of the outlets comprises a hole in a layer to which the sticker means is adherable.

5. The apparatus according to claim 1, wherein one or more of the outlets comprises a clearance between one or more outlets, or weld segments.

6. The apparatus according to claim 1, further comprising a flow restricting layer provided upstream of the outlets.

7. The apparatus according to claim 1, wherein the vent includes aperture means having a plurality of apertures for outletting gas through said vent, and a flow restricting layer upstream of the aperture means.

8. The apparatus according to claim 7, wherein the aperture means comprises a plurality of individual vent apertures.

9. The apparatus according to claim 7, wherein the sticker means comprises a plurality of stickers or sticker segments.

10. The apparatus according to claim 7, wherein the sticker means is positioned or positionable to selectively block all of the area of the aperture means.

11. The apparatus according to claim 7, wherein the flow restricting layer comprises microporous material.

12. The apparatus according to claim 7, wherein the pouch comprises a first wall provided with the vent and with a comfort layer.

13. The apparatus according to claim 1, further comprising an adhesive wafer for securing the pouch to a person's skin, wherein the wafer, or a cover layer provided on the wafer, is provided with guidelines for enabling a person to cut the wafer to a desired aperture size, the guidelines including at least one generally circular guideline and at least one generally non-circular guideline.

14. The apparatus according to claim 7, further comprising an adhesive wafer for securing the pouch to a person's skin, wherein the wafer, or a cover layer provided on the wafer, is provided with guidelines for enabling a person to cut the wafer to a desired aperture size, the guidelines including at least one generally circular guideline and at least one generally non-circular guideline.

15. The apparatus according to claim 1, wherein a plurality of the circular guidelines and plurality of the non-circular guidelines are provided.

16. An apparatus comprising a controllable flow rate, filtered, vent for an ostomy pouch, the vent having a plurality of outlets and a device for controlling the rate of flow of gas through the vent, the device comprising adhesive sticker means which can be positioned and re-positioned to selectively expose or cover one or more of the plurality of outlets, and thereby regulate variably the rate of flow of gas according to the outlets exposed, and a body-side device for attachment to an ostomy pouch, the body-side device comprising an adhesive wafer for directly or indirectly securing the ostomy pouch to a person's skin, and a coupling portion for releasable fastening to the pouch, wherein the wafer, or a cover layer provided on the wafer, is provided with guidelines for enabling a person to cut the wafer to a desired aperture size, the guidelines including at least one generally circular guideline, and at least one generally non-circular guideline, and wherein the wafer is secured to the coupling portion around a closed loop line of attachment, the line of attachment is defined by a combination of a circular shape and a race-track shape, the combined shape corresponding to a silhouette of one superimposed on the other.

* * * * *